United States Patent [19]

Krag et al.

[11] Patent Number: 5,741,255

[45] Date of Patent: Apr. 21, 1998

[54] SPINAL COLUMN RETAINING APPARATUS

[75] Inventors: Martin H. Krag, Colchester, Vt.; Craig Glascott, Twinsburg, Ohio

[73] Assignee: AcroMed Corporation, Cleveland, Ohio

[21] Appl. No.: 658,749

[22] Filed: Jun. 5, 1996

[51] Int. Cl.⁶ .................................................. A61B 17/70
[52] U.S. Cl. .................................................. 606/61; 606/73
[58] Field of Search .................................. 606/61, 60, 72, 606/73, 59, 86

[56]  References Cited

U.S. PATENT DOCUMENTS

| | | |
|---|---|---|
| 4,987,892 | 1/1991 | Krag et al. . |
| 5,002,542 | 3/1991 | Frigg . |
| 5,053,034 | 10/1991 | Olerud . |
| 5,129,900 | 7/1992 | Asher et al. . |
| 5,254,118 | 10/1993 | Mirkovic . |
| 5,257,993 | 11/1993 | Asher et al. . |
| 5,261,909 | 11/1993 | Sutterlin et al. . |
| 5,306,275 | 4/1994 | Bryan . |
| 5,403,316 | 4/1995 | Ashman . |
| 5,474,551 | 12/1995 | Finn et al. .................... 606/61 |
| 5,487,744 | 1/1996 | Howland ...................... 606/61 |
| 5,499,983 | 3/1996 | Hughes ........................ 606/61 |
| 5,527,314 | 6/1996 | Brumfield et al. ............ 606/61 |
| 5,624,441 | 4/1997 | Sherman et al. ............. 606/61 |

FOREIGN PATENT DOCUMENTS 9513756  5/1995  WIPO .

*Primary Examiner*—Guy V. Tucker
*Attorney, Agent, or Firm*—Tarolli, Sundheim, Covell, Tummino & Szabo

[57]  ABSTRACT

An apparatus for retaining vertebrae in a desired spatial relationship. The apparatus includes a fastener which cooperates with a connector assembly, a longitudinal member which is positionable along the spinal column at a location offset from the fastener, and a connector assembly which connects the fastener with the longitudinal member. The connector assembly includes a transverse member, a retainer block, and a set screw. The transverse member and retainer block have mating teeth. When the desired spatial relationship is achieved, the set screw is tightened thereby engaging the teeth and providing for a rigid locked assembly.

2 Claims, 5 Drawing Sheets

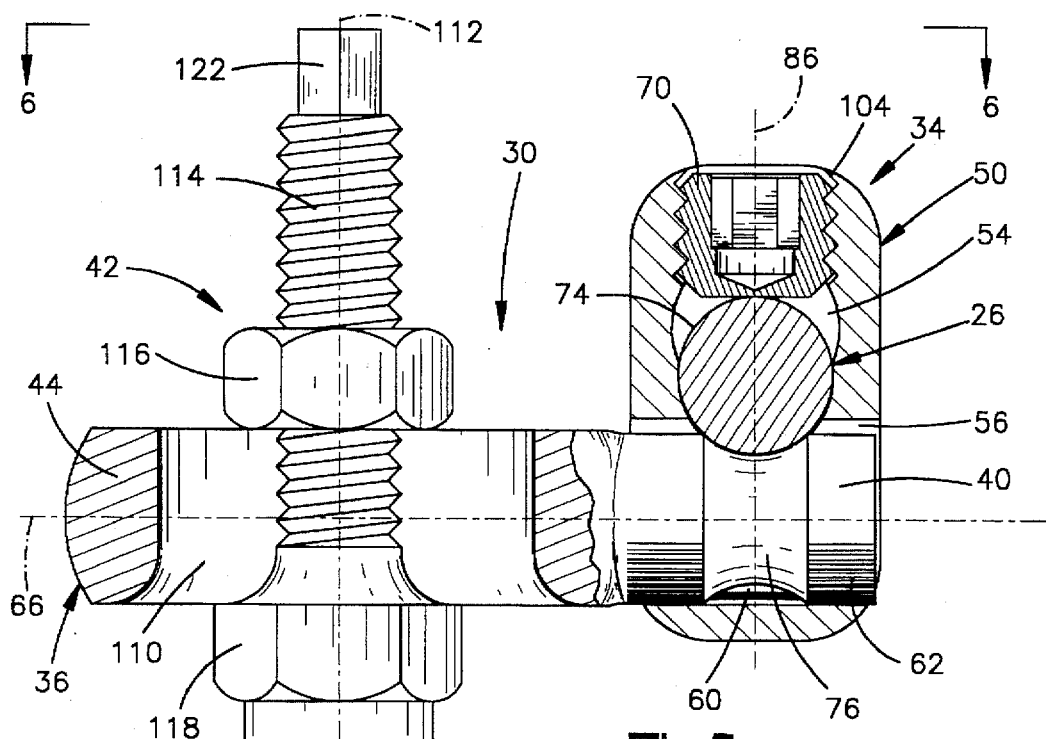
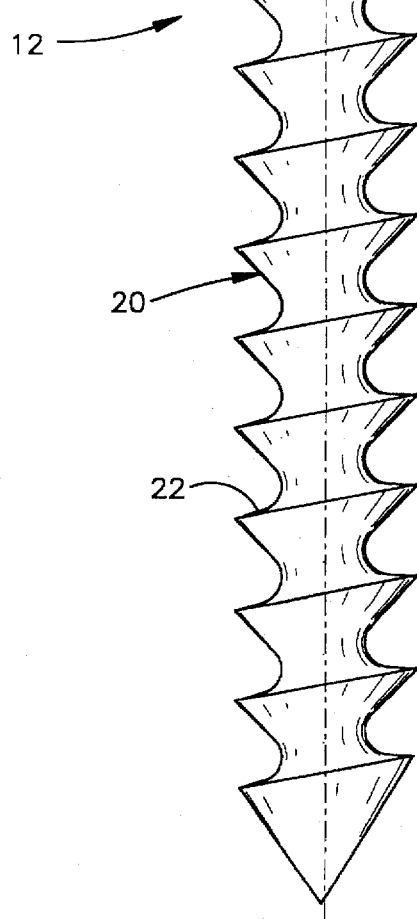
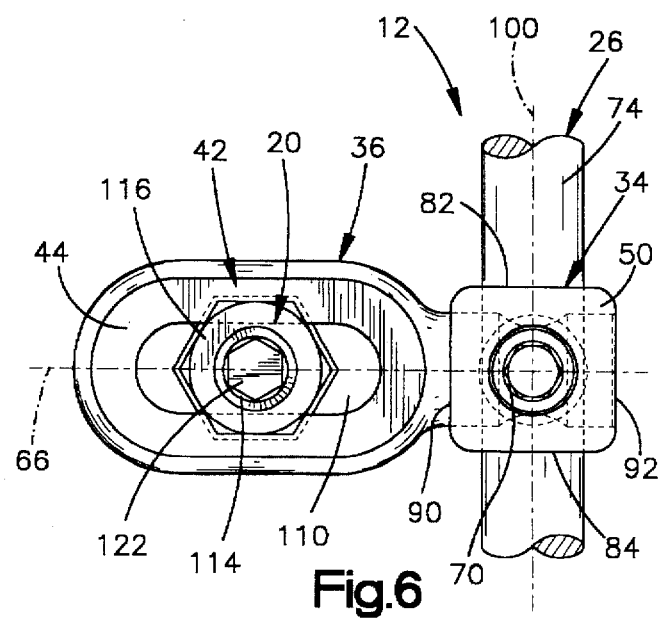
Fig. 5
Fig. 6

SPINAL COLUMN RETAINING APPARATUS

BACKGROUND OF THE INVENTION

The present invention relates to an apparatus which is used to retain portions of a spinal column, such as vertebrae in a desired spatial relationship.

A known apparatus for retaining vertebrae in a desired spatial relationship is disclosed in U.S. Pat. No. 5,129,900. This known apparatus includes a fastener having a threaded end portion which engages a vertebra. A connector assembly interconnects the fastener and a longitudinal member, such as a rod, which extends substantially parallel to the axis of the spine. The connector assembly is adjustable to enable the distance between the longitudinal member and the fastener to be varied while the fastener remains stationary relative to the vertebra to which it is connected. Other known apparatus for retaining vertebrae in a desired spatial relationship are disclosed in U.S. Pat. Nos. 5,053,034; 5,254,118; 5,257,993; and 5,306,275.

SUMMARY OF THE INVENTION

The present invention provides a new and improved apparatus for retaining portions of a spinal column in a desired spatial relationship. The apparatus includes a fastener having a threaded end portion which engages a portion of the spinal column and a longitudinal member which is positioned along the spinal column at a location offset from the fastener. A transverse member is connected with the fastener and extends transversely to a central axis of the longitudinal member.

An improved retainer assembly is provided to retain the transverse member against movement relative to the longitudinal member. The retainer assembly includes a retainer block into which the longitudinal member and the transverse member extend. The retainer assembly is effective to hold the transverse member against movement relative to the retainer block due to force transmitted between the transverse member and the longitudinal member. In one embodiment of the invention, the force is transmitted between the longitudinal member and the transverse member by pressing them against each other with a set screw.

The retainer block may advantageously be provided with retainer surfaces which are engaged by retainer surfaces on the transverse member. The retainer surfaces on the retainer block and the retainer surfaces on the transverse member cooperate to retain the transverse member against rotation about a central axis of the transverse member.

BRIEF DESCRIPTION OF THE DRAWINGS

The foregoing and other features of the invention will become more apparent upon a consideration of the following description taken in connection with the accompanying drawings, wherein:

FIG. 5 is a sectional view, taken generally along the line 5—5 of FIG. 4, further illustrating the construction of a portion of the apparatus;

FIG. 6 is a plan view, taken on a reduced scale along the line 6—6 of FIG. 5, further illustrating the construction of a portion of the apparatus;

DESCRIPTION OF SPECIFIC PREFERRED EMBODIMENTS OF THE INVENTION

General Description

Figure 1:
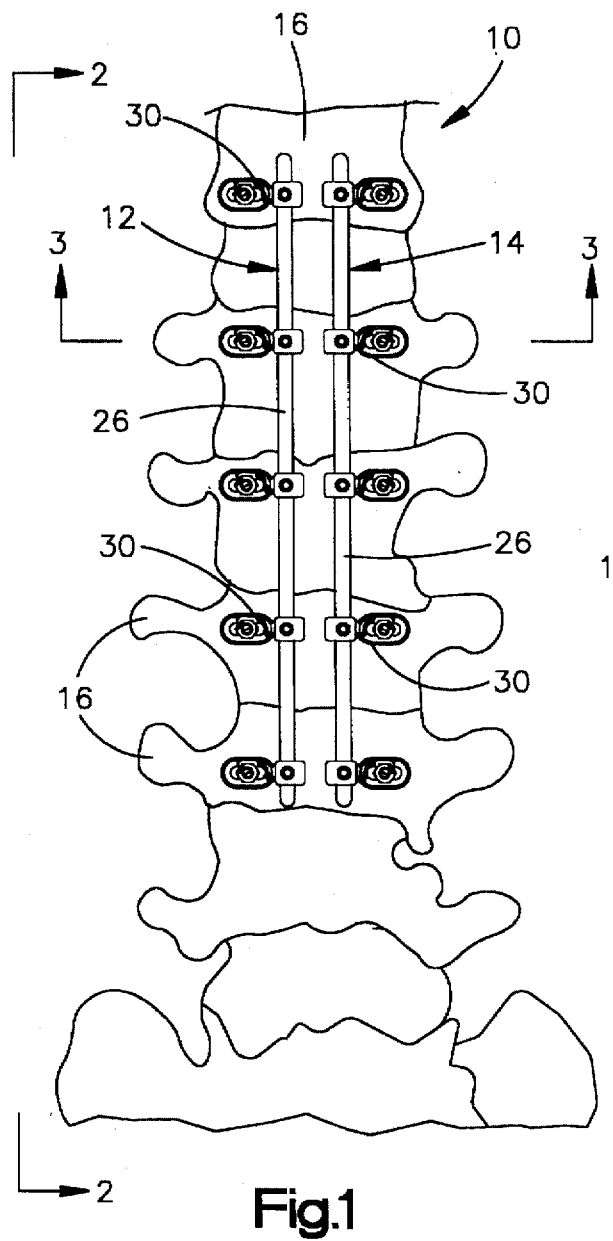
FIG. 1 is a dorsal view of a portion of a spinal column with the spinal column retaining apparatus of the present invention to maintain a desired spatial relationship between vertebrae of the spinal column.
Figure 2:
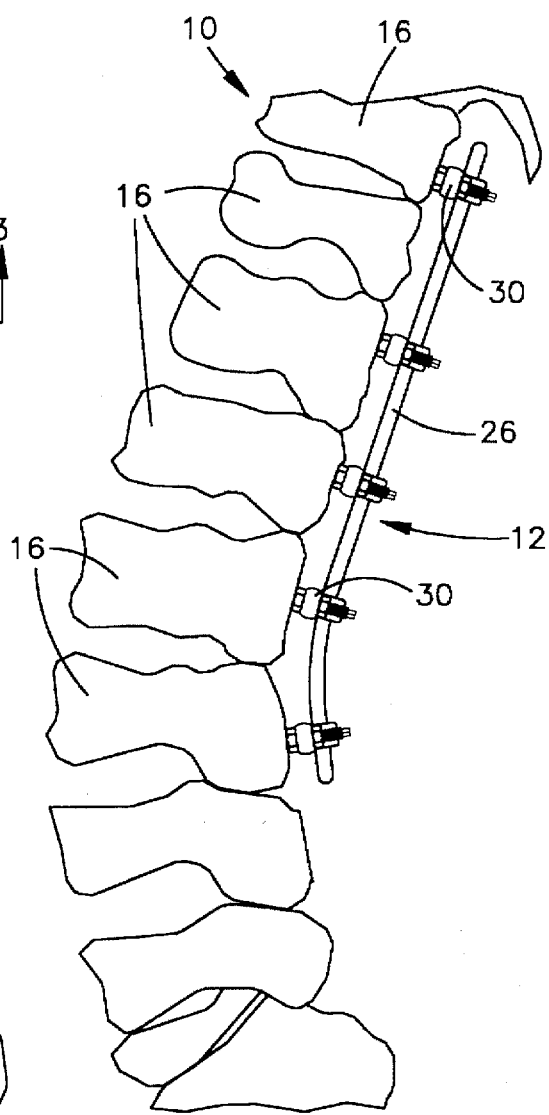
FIG. 2 is a sagittal view of the spinal column of FIG. 1, further illustrating the manner in which vertebrae of the spinal column are held in the desired spatial relationship.
Figure 3:
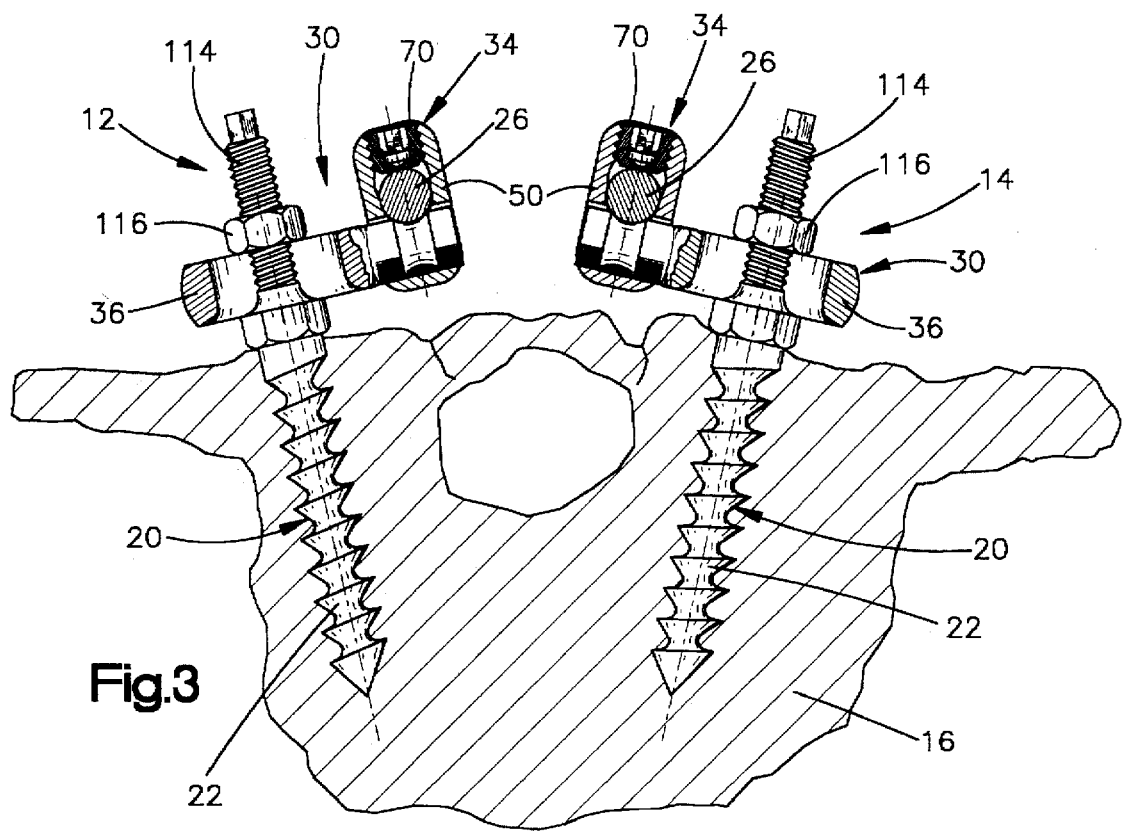
FIG. 3 is a sectional view, taken generally along the line 3—3 of FIG. 1, illustrating the manner in which the apparatus is connected with a vertebra.

A human spinal column 10 to which spinal column retaining apparatuses 12 and 14 are connected is illustrated in FIGS. 1–3. The spinal column retaining apparatuses 12 and 14 position portions of the spinal column 10, that is vertebrae 16, in a desired spatial relationship relative to each other.

The spinal column retaining apparatuses 12 and 14 have the same construction and include fasteners 20 (FIG. 3) made of a biocompatible material, such as stainless steel. The fasteners 20 have threaded inner end portions 22 which engage vertebrae 16 to fixedly mount the fasteners in the vertebrae. Usually there are a pair of fasteners 20 for each vertebrae, as shown in FIG. 3. It should be understood that there could be more or fewer than that. In FIGS. 1 and 2, five pairs of fasteners 20 are connected with five vertebrae 16 of the spinal column 10. It should be understood that there is no specific upper or lower limit to the number of vertebrae involved.

The spinal column retaining apparatuses 12 and 14 include a longitudinal member, such as the depicted cylindrical rod 26, which extends along the spinal column 10. Each of the longitudinal members or rods 26 is made of a biocompatible material, such as stainless steel. Each of the rods 26 has a length sufficient to enable the rod to span at least two of the vertebrae 16. In the embodiment of the invention illustrated in FIGS. 1 and 2, the rods 26 span six vertebrae 16. Of course, the length of the rod in any particular apparatus will depend upon the condition to be corrected and the number of vertebrae 16 to be held in a desired spatial relationship relative to each other by the apparatus. The rods 26 may be bent as desired, typically to conform to a desired curvature of the spinal column 10 in all or any of three possible anatomic planes.

The apparatus 12 includes a connector assembly 30 which is constructed in accordance with the present invention and interconnects the rod 26 and a fastener 20. The connector assembly 30 includes an improved retainer assembly 34 which is mounted on the rod 26. In addition, the connector assembly 30 includes a transverse member 36 which extends between the fastener 20 and the retainer assembly 34. The retainer assembly 34 fixedly connects a generally cylindrical inner end portion 40 (FIG. 5) of the transverse member 36 with the rod 26. A clamp assembly 42 fixedly connects a slotted outer end portion 44 of the transverse member 36 with the fastener 20.

The retainer assembly 34 includes a set screw 70 and a generally rectangular retainer block 50 into which the transverse member 36 and rod 26 extend. The retainer block 50 has a rod passage 54 (FIGS. 5, 7 and 8) through which the rod 26 extends. In addition, the retainer block 50 has a transverse passage 56 through which the inner end portion 40 of the transverse member 36 extends.

Figure 7:
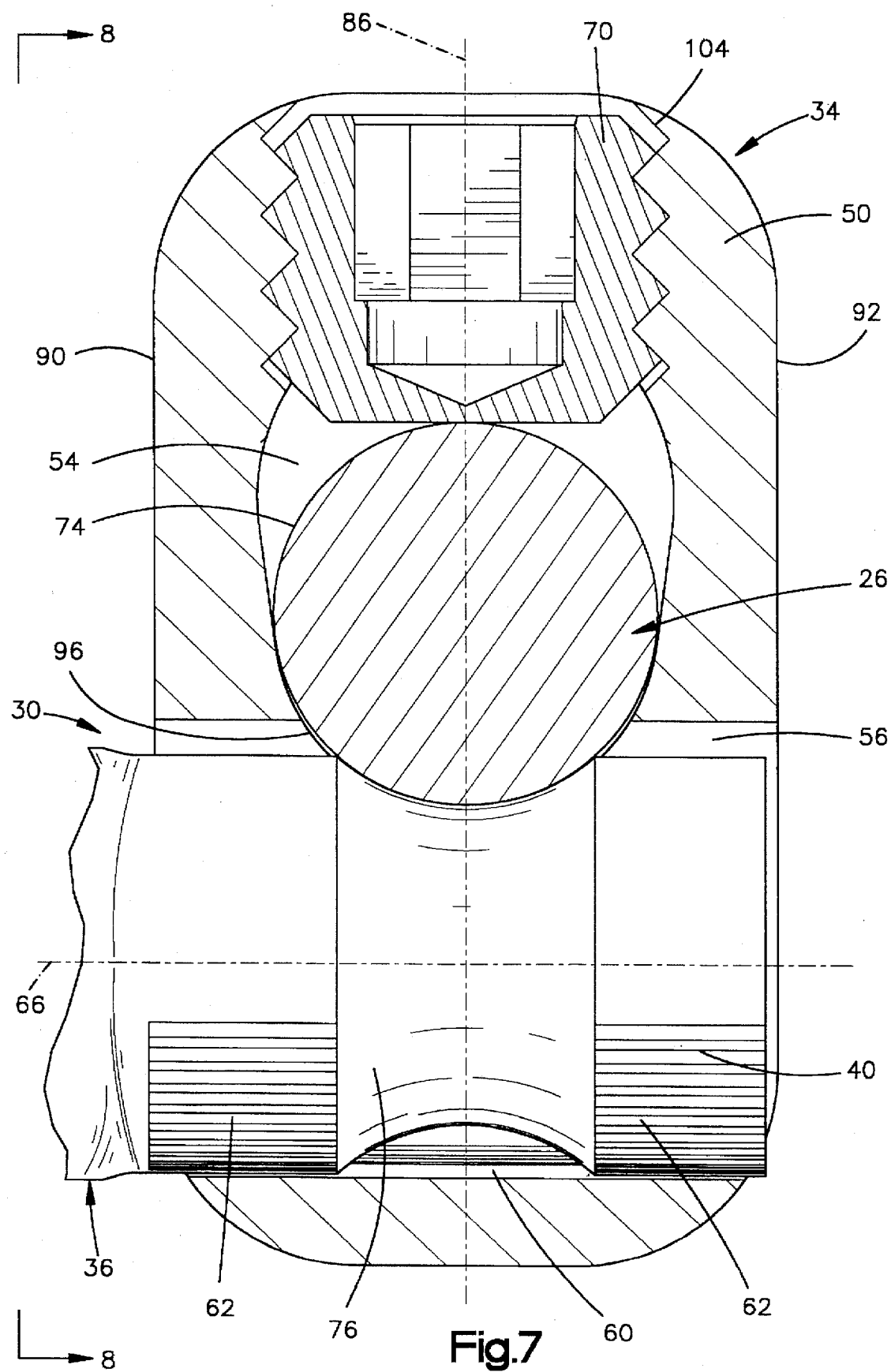
FIG. 7 is an enlarged fragmentary sectional view of a portion of FIG. 5 and illustrating the relationship between a transverse member, a longitudinal member, and a retainer assembly in the apparatus.

In accordance with a feature of the present invention, the transverse passage 56 has a plurality of inwardly projecting retainer surfaces or teeth 60 (FIG. 8) which engage retainer surfaces or teeth 62 (FIG. 7) on the inner end portion 40 of the transverse member 36. Meshing engagement between the teeth 60 on the retainer block 50 and the teeth 62 on the transverse member 36 hold the transverse member against rotation about its longitudinal central axis 66 relative to the retainer block 50 (FIGS. 5 and 7).

In accordance with another feature of the present invention, force is transmitted between the transverse member 36 and the rod 26 to hold the transverse member 36 against movement relative to the retainer block 50. Thus, the set screw 70 presses the rod 26 downward (as viewed in FIG. 7) against the transverse member 36. This presses the teeth 62 on the transverse member into tight meshing engagement with the teeth 60 on the lower portion of the transverse passage 56 in the retainer block 50. Engagement of a cylindrical outer side surface 74 on the rod 26 with an annular groove 76 on the inner end portion 40 of the transverse member 36 retains the transverse member against movement relative to the retainer block 50 along the central axis 66 of the transverse member 36.

Retainer Assembly

Figure 8:
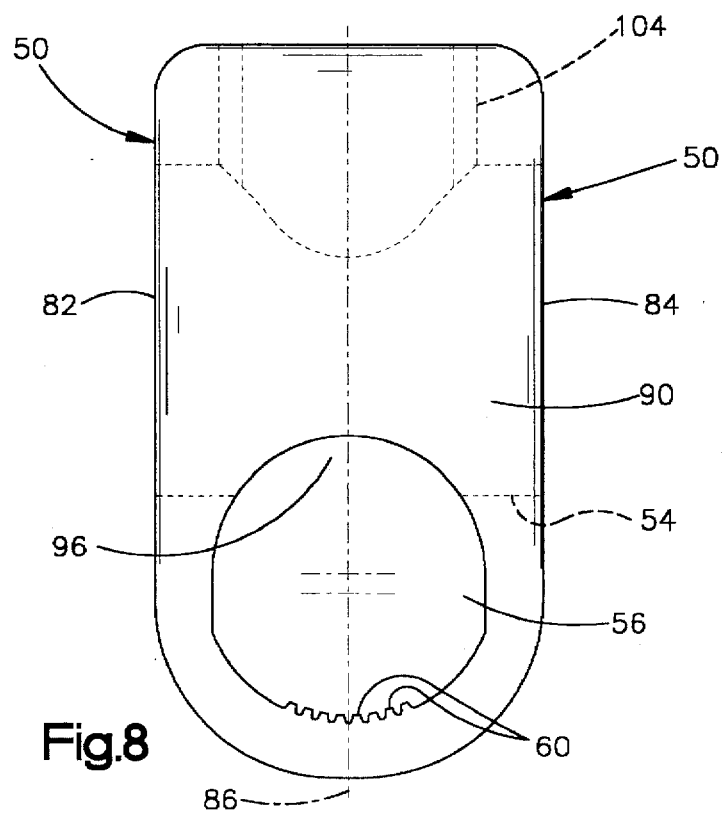
FIG. 8 (on sheet 2 of the drawings) is an enlarged side elevational view, taken generally along the line 8—8 of FIG. 7, illustrating the construction of a retainer block in the apparatus.
Figure 4:
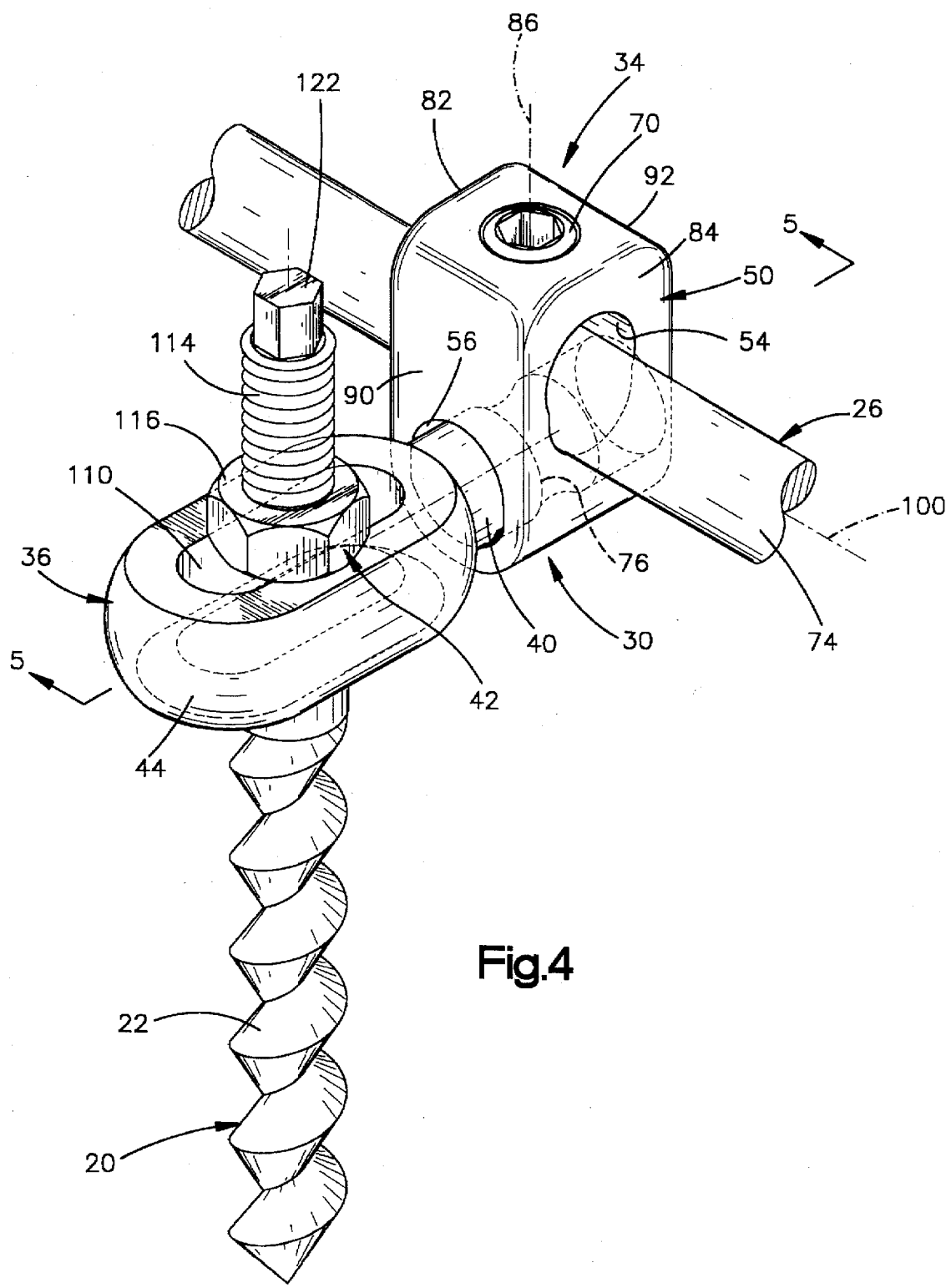
FIG. 4 is an enlarged pictorial illustration of a portion of the apparatus of FIGS. 1–3.

The retainer block 50 has a pair of parallel flat side surfaces 82 and 84 (FIGS. 4, 6 and 8). The rod passage 54 (FIG. 7) extends between and is perpendicular to the parallel side surfaces 82 and 84 (FIG. 6). The rod passage 54 has a straight longitudinal central axis which extends parallel to side surfaces 90 and 92 (FIG. 7). The side surfaces 90 and 92 extend perpendicular to the side surfaces 82 and 84 (FIGS. 4, 6 and 8).

The rod passage 54 is formed by a pair of circular openings having centers which are offset along a central axis 86 (FIG. 7) of the retainer block 50. This results in the rod passage 54 having a generally oval cross sectional configuration. The size of the circular openings which cooperate to form the rod passage 54 are such that the rod 26 can move between the upper (as viewed in FIG. 7) and lower portion of the rod passage 54. In fact, the lower circular opening in FIG. 7 has a smaller diameter than the diameter of the rod 26. Thus, the rod 26 and retainer block 50 have an interference fit when the rod 26 is in the lower circular opening in FIG. 7.

The transverse passage 56 extends between and is perpendicular to the parallel side surfaces 90 and 92 (FIGS. 4, 6, 7 and 8). Like the rod passage 54, the transverse passage 56 has a generally oval cross sectional configuration. The transverse passage 56 is formed by a pair of cylindrical openings having centers which are offset along the central axis 86 of the retainer block 50 (FIG. 8).

The diameters of the cylindrical openings forming the transverse passage 56 are large enough to enable the teeth 62 on the transverse member 36 (FIG. 7) to be spaced away from the teeth 60 (FIG. 8) when the transverse member 36 engages an upper (as viewed in FIGS. 7 and 8) portion of the transverse passage 56. This enables the transverse member 36 to be rotated about its central axis 66 to a desired position relative to the retainer block 50 and the rod 26. Once the transverse member 36 has been rotated to a desired orientation about the axis 66, the transverse member is moved downward (as viewed in FIG. 7) to move the teeth 62 on the transverse member into meshing engagement with the teeth 60 on the retainer block 50.

The transverse passage 56 and rod passage 54 have an intersection 96 (FIG. 8) in a central portion of the retainer block 50. Thus, a portion of the transverse passage 56 extends into the rod passage 54 and a portion of the rod passage extends into the transverse passage. In the illustrated embodiment of the invention, the rod passage 54 has a central axis which extends perpendicular to the central axis of the transverse passage 56. This results in the central axis 66 of the transverse member 36 extending perpendicular to the a central axis 100 of the rod 26 (FIG. 6). However, the transverse passage 56 could be skewed at an acute angle relative to the rod passage 54. This would result in the transverse member 36 having a central axis 66 which extends at an acute angle relative to the central axis 100 of the rod 26.

When the retainer block 50 is positioned on the rod 26, in the manner illustrated in FIGS. 4–7, the rod extends into the intersection 96 (FIGS. 7 and 8) between the rod passage 54 and the transverse passage 56. This enables the cylindrical outer side surface 74 of the rod 26 (FIG. 7) to be pressed against the annular groove 76 in the inner end portion 40 of the transverse member 36 by the set screw 70. The transverse member 36 is pressed against the lower (as viewed in FIG. 7) portion of the retainer block 50 by the rod 26. If desired, an intermediate force transmitting member could be provided between the rod 26 and the transverse member 36.

The set screw 70 is disposed in an internally threaded set screw passage 104 disposed in the retainer block 50. The central axis of the set screw passage 104 is parallel with the central axis 86 of the retainer block 50 and is aligned with the center of the intersection 96 between the rod passage 54 and transverse passage 56. The central axis of the set screw 70 extends perpendicular to and intersects the central axis 100 of the rod 26 and the central axis 66 of the transverse member 36 (FIGS. 5–7).

When the set screw 70 is tightened in the set screw passage 104, force is transmitted from the set screw to the rod 26 along the central axis of the set screw. This force is transmitted directly from the rod 26 to the transverse member 36 at the intersection 96 between rod passage 54 and the transverse passage 56. Thus, the outer side surface 74 of the rod 26 is pressed against the surface of the annular groove 76 in the transverse member 36. The force is transmitted through the transverse member 36 to the retainer block 50.

The teeth 60 (FIG. 8) on the retainer block 50 project into the transverse passage 56. The teeth 60 are disposed on a side of the transverse passage 56 opposite from the intersection 96 between the transverse passage and the rod passage 54. The teeth 60 have an arcuate extent of approximately 30° on each side of the central axis 86 of the retainer block 50. Thus, the teeth 60 have a total arcuate extent of approximately 60° about the center of the cylindrical opening forming the lower portion of the transverse passage 56. The teeth 60 have straight longitudinal central axes which extend parallel to the central axis of the transverse passage 56 and to the opposite side surfaces 82 and 84 of the retainer block 50. When the transverse member 36 is positioned in the transverse passage 56 (FIG. 7), the teeth 62 on the transverse member 36 are disposed in meshing engagement with the teeth 60 on the retainer block 50.

Transverse Member

The transverse member 36 (FIGS. 4, 5 and 6) has inner and outer end portions 40 and 44 (FIG. 5). The inner end portion 40 of the transverse member 36 has a generally cylindrical configuration. Each of the teeth 62 on the inner end portion 40 of the transverse member 36 has a longitudinal central axis which extends parallel to the central axis 66 of the transverse member. The plurality of teeth 62 have an arcuate extent of approximately 120° about the central axis 66 of the transverse member 36. However, the teeth 62 may be generated along the entire circumference of the transverse member 36.

Since the arcuate extent of the plurality of teeth 62 on the inner end portion 40 of the transverse member 36 is greater than the arcuate extent of the plurality of teeth 60 (FIG. 8) on the retainer block 50, the teeth 62 on the transverse member 36 can meshingly engage the teeth 60 on the retainer block 50 when the transverse member is at any one of a plurality of rotational orientations relative to the retainer block. The transverse member 36 can be rotated about its central axis 66 relative to the retainer block 50 when the transverse member is displaced upward (as viewed in FIG. 7) toward the upper portion of the transverse passage 56.

When the transverse member 36 has been rotated to a desired orientation relative to the retainer block 50, the transverse member is moved downward to move the teeth 62 on the transverse member 36 into meshing engagement with the teeth 60 on the retainer block 50. Force transmitted from the set screw 70 through the rod 26 to the transverse member 36, firmly presses the teeth 62 on the transverse member against the teeth 60 on the retainer block 50. Although it is preferred to have the rod 26 disposed in engagement with the transverse member 36, an intermediate force transmitting member could be provided between the rod and transverse member if desired.

The outer end portion 44 of the transverse member 36 is provided with a slot 110 (FIGS. 5 and 6). The slot 110 has a central axis which is coincident with the central axis 66 of the transverse member. The fastener 20 extends through the slot 110 in the outer portion 44 of the transverse member 36. The clamp assembly 42 clamps the transverse member 36 against movement relative to the fastener 20. When the clamp assembly 42 is engaged, a central axis 112 of the fastener extends perpendicular to and intersects the central axis 66 of the transverse member 36.

The clamp assembly 42 is formed by a threaded outer end portion 114 of the fastener 20, an internally threaded nut 116, and a hexagonal shoulder 118 formed on the fastener (FIG. 5). A hexagonal outer end portion 122 of the fastener 20 is engageable by a wrench. At the same time, the nut 116 is engageable by a wrench. This enables the nut 116 to be firmly tightened on the externally threaded outer portion 114 of the fastener 20 without transmitting force to the threaded inner end portion 22 of the fastener 20. The slot 110 allows the distance between the central axis 112 of the fastener 20 and the central axis 86 of the retainer block 50 to be varied to suit the characteristics of the particular location in which the connector assembly 30 is disposed along the spinal column 10.

In the illustrated embodiment of the transverse member 36, the slot 110 accommodates variations in the distance between the fastener and the longitudinal member or rod 26. However, it is contemplated that the transverse member 36 could be formed by a straight projection which does not have a slot and extends into a clamp assembly connected with an end portion of the fastener 20 if desired.

Conclusion

The present invention provides a new and improved apparatus 12 for use in retaining portions 16 of a spinal column 10 in a desired spatial relationship. The apparatus includes a fastener 20 having a threaded end portion 22 which engages a portion 16 of the spinal column and a longitudinal member 26 which is positioned along the spinal column 10 at a location offset from the fastener 20. A transverse member 36 is connected with the fastener 20 and extends transversely to a central axis 100 of the longitudinal member 26.

An improved retainer assembly 34 is provided to retain the transverse member 36 against movement relative to the longitudinal member 26. The retainer assembly 34 includes a retainer block 50 into which the longitudinal member 26 and the transverse member 36 extend. The retainer assembly 34 is effective to hold the transverse member 36 against movement relative to the retainer block 50 due to force transmitted between the transverse member 36 and the longitudinal member 26. In one embodiment of the invention, the force is transmitted between the longitudinal member 26 and the transverse member 36 by pressing them against each other.

The retainer block 50 may advantageously be provided with a plurality of retainer surfaces or teeth 60 which are engaged by retainer surfaces or teeth 62 on the transverse member 36. The teeth 60 on the retainer block 50 and the teeth 62 on the transverse member 36 cooperate to retain the transverse member against rotation about the central axis 66 of the transverse member.

Having described the invention, the following is claimed:

1. An apparatus for use in retaining portions of a spinal column of a patient in a desired spatial relationship, said apparatus comprising:

a fastener having a thread convolution for threadly engaging a portion of the spinal column, said fastener having a first axis and being rotatable about said first axis;

a longitudinal member which is implantable along the spinal column of the patient at a location offset from said fastener, said longitudinal member having a second axis;

a transverse member having a first portion with an opening through which a portion of said fastener extends, said portion of said fastener being coaxial with said thread convolution, said transverse member having a second portion connectable with said longitudinal member, said transverse member extending transverse to said first and second axes when connected with said fastener and said longitudinal member; and a retainer block having a first opening portion into which said longitudinal member extends and a second opening portion into which said transverse member extends, said first and second opening portions communicating with each other and having third and fourth axes perpendicular to each other;

said retainer block also having a threaded opening communicating with said first opening portion;

said retainer block and transverse member being relatively rotatable between a plurality of relative positions when said transverse member is in said second opening portion;

said retainer block including a first plurality of retainer teeth;

said transverse member including a second plurality of retainer teeth which are disposed out of engagement with said first plurality of retainer teeth when said retainer block and said transverse member relatively rotate, said first and second plurality of retainer teeth when engaged blocking relative rotation of said retainer block and said transverse member; and a set screw for screwing into said threaded opening in said retainer block and engaging said longitudinal member to force said longitudinal member and said transverse member into engagement with each other and to hold said first and second plurality of retainer teeth in engagement to prevent relative rotation of said retainer block and said transverse member after said retainer block and said transverse member have been positioned in one of said plurality of relative positions;

said second portion of said transverse member being circular in cross section, said second plurality of retainer teeth extending from said circular cross section of said transverse member transverse to said third axis, said first plurality of retainer teeth extending from a surface of said retainer block defining said second opening transverse to said third axis.

2. An apparatus as defined in claim 1 wherein said second portion of said transverse member has a surface which is curved axially and defines a groove extending circumferentially around said second portion of said transverse member and said longitudinal member has a cylindrical outer surface extending around said second axis and which is forced by said set screw into engagement with said surface on said transverse member which is curved axially.

\* \* \* \* \*